(12) United States Patent
Chen et al.

US010758584B2

(10) Patent No.: US 10,758,584 B2
(45) Date of Patent: Sep. 1, 2020

(54) TOPICAL FORMULATION FOR PROMOTING WOUND HEALING

(71) Applicant: Oneness Biotech Co. LTD, Taipei (TW)

(72) Inventors: Jen-Wei Chen, Taipei (TW); Kung-Ming Lu, Taipei (TW)

(73) Assignee: Oneness Biotech Co. LTD, Taipei (TW)

( * ) Notice: Subject to any disclaimer, the term of this patent is extended or adjusted under 35 U.S.C. 154(b) by 372 days.

(21) Appl. No.: 15/651,337

(22) Filed: Jul. 17, 2017

(65) Prior Publication Data

US 2018/0015133 A1 Jan. 18, 2018

Related U.S. Application Data

(60) Provisional application No. 62/363,284, filed on Jul. 17, 2016.

(51) Int. Cl.
| | |
|---|---|
| *A61K 36/53* | (2006.01) |
| *A61K 9/00* | (2006.01) |
| *A61K 9/06* | (2006.01) |
| *A61K 9/107* | (2006.01) |
| *A61K 31/353* | (2006.01) |
| *A61K 31/704* | (2006.01) |
| *A61K 36/23* | (2006.01) |
| *A61K 47/10* | (2017.01) |
| *A61K 47/46* | (2006.01) |

(52) U.S. Cl.
CPC ............ *A61K 36/53* (2013.01); *A61K 9/0014* (2013.01); *A61K 9/06* (2013.01); *A61K 9/107* (2013.01); *A61K 31/353* (2013.01); *A61K 31/704* (2013.01); *A61K 36/23* (2013.01); *A61K 47/10* (2013.01); *A61K 47/46* (2013.01)

(58) Field of Classification Search
None
See application file for complete search history.

(56) References Cited

U.S. PATENT DOCUMENTS

| | | |
|---|---|---|
| 4,318,906 A | 3/1982 | Llopart |
| 5,834,437 A | 11/1998 | Jew et al. |
| 6,267,996 B1 | 7/2001 | Bombardelli et al. |
| 6,417,349 B1 | 7/2002 | Kim et al. |
| 6,475,536 B2 | 11/2002 | Bombardelli et al. |
| 6,579,543 B1 | 6/2003 | McClung |
| 6,673,377 B1 * | 1/2004 | Cherdshewasart ...... A61K 8/97 424/725 |
| 7,531,194 B2 | 5/2009 | Wu et al. |
| 7,985,431 B2 | 7/2011 | Wu et al. |
| 8,247,004 B2 | 8/2012 | Wu et al. |
| 8,449,924 B2 | 5/2013 | Wu et al. |
| 2006/0099283 A1 | 5/2006 | Wei et al. |
| 2014/0322365 A1 * | 10/2014 | Ko ...................... A61K 31/353 424/745 |
| 2017/0273938 A1 | 9/2017 | Chang et al. |

FOREIGN PATENT DOCUMENTS

| | | |
|---|---|---|
| CN | 1089497 A | 7/1994 |
| CN | 1137681 A | 12/1996 |
| CN | 1194154 A | 9/1998 |
| CN | 1313124 A | 9/2001 |
| CN | 1353972 A | 6/2002 |
| CN | 1682744 A | 10/2005 |
| CN | 101375933 A | 3/2009 |
| CN | 103127215 | 6/2013 |
| CN | 103420967 A | 12/2013 |
| JP | 200459482 A | 2/2004 |
| JP | 2009078062 A | 4/2009 |
| WO | WO 2016/033802 A1 | 3/2016 |

OTHER PUBLICATIONS

"BioPortfolio.com" ("The Pharmacokinetic Study of WH-1 Ointment in Subjects with Chronic Diabetic Foot Ulcers." (May 5, 2011) Retrieved from https://www.bioportfolio.com/resources/trial/137253/The-Pharmacokinetic-Study-of-WH-1-Ointment-in-Subjects-With-Chronic-Diabetic.html ).*
[No Author Listed] Clinical Evaluation of DCB-WH1 in Healing of Chronic Diabetic Foot Ulcers. Clinical Trials. Jul. 3, 2008. Last accessed Feb. 6, 2018 at https://clinicaltrials.gov/ct2/show/NCT00709514?term=wh-1&rank=3.
[No Author Listed] Evaluate the Efficacy and Safety of WH-1 Ointment for the Treatment of Chronic Diabetic Foot Ulcers (WH-1). Clinical Trials. Jul. 15, 2013. Last accessed Feb. 6, 2018 at https://clinicaltrials.gov/ct2/show/NCT01898923?term=on101&rank=2.
[No Author Listed] The Pharmacokinetic Study of WH-1 Ointment in Subjects With Chronic Diabetic Foot Ulcers. Clinical Trials. Feb. 2, 2015. Last accessed Feb. 6, 2018 at https://clinicaltrials.gov/ct2/show/NCT02353273?term=on101&rank=1.
[No Author Listed], ON101 has been approved by CFDA. Oneness Biotech. Jul. 19, 2017. Last accessed Feb. 6, 2018 at https://www.onenessbio.com.tw/en/news_detail.php?nwno=261.
[No Author Listed], Oneness Biotech Announce the Phase III Clinical Trials Results Today. Oneness Biotech. Jul. 18, 2016. Last accessed Feb. 6, 2018 at https://www.onenessbio.com.tw/en/news_detail.php?nwno=251.
[No Author Listed], Oneness Biotech's Investigational New Drug ON101 Approved for Clinical Pharmacokinetic Studies by Ministry of Health and Welfare. Oneness Biotech. Jan. 22, 2015. Last accessed Feb. 6, 2018 at https://www.onenessbio.com.tw/en/news_detail.php?nwno=237.
[No Author Listed], Oneness Biotech's New Drug ON101 for Treatment of Chronic Diabetic Foot Ulcers Approved for Phase III Human Clinical Trials by Hong Kong Department of Health. Oneness Biotech. Dec. 3, 2014. Last accessed Feb. 6, 2018 at https://www.onenessbio.com.tw/en/news_detail.php?nwno=240.

(Continued)

*Primary Examiner* — Susan Hoffman
(74) *Attorney, Agent, or Firm* — Polsinelli PC (57) ABSTRACT

The present invention provides a topical formulation comprising an active agent, which comprises salvigenin and optionally asiaticoside. The present invention also relates to the use of the topical formulation for the promotion of wound healing.

19 Claims, 7 Drawing Sheets

(56) References Cited

OTHER PUBLICATIONS

[No Author Listed], The New Drugs ON101 (WH-1) of Oneness Biotech Meet the Phase III Clinical Trials Interim Requirement and is going to initiate Phase III Clinical Trials in China and EU. Oneness Biotech. Jul. 19, 2016. Last accessed Feb. 6, 2018 at https://www.onenessbio.com.tw/en/news_detail.php?nwno=252.

[No Author Listed], The New Drugs ON101 (WH-1) of Oneness Biotech Successively Pass the Blind Test. Oneness Biotech. Jul. 19, 2016. Last accessed Feb. 6, 2018 at https://www.onenessbio.com.tw/en/news_detail.php?nwno=253.

[No Author Listed], The World's Best New Drug's Healing Rate of Oneness Biotech is Accelerating Product Launch. Oneness Biotech. Jul. 18, 2016. Last accessed Feb. 6, 2018 at https://www.onenessbio.com.tw/en/news_detail.php?nwno=250.

Arumugam et al., Plectranthus amboinicus (Lour.) Spreng: Botanical, Phytochemical, Pharmacological and Nutritional Significance. Molecules. Mar. 30, 2016;21(4):369. doi: 10.3390/molecules21640369.

Alvin et al., Modulatory effect of Plectranthus amboinicus Lour. on ethylene glycol-induced nephrolithiasis in rats. Indian J Pharmacol 2005;37:43-4.

* cited by examiner

TOPICAL FORMULATION FOR PROMOTING WOUND HEALING

CROSS REFERENCE TO RELATED APPLICATIONS

This application claims the benefit of the filing date of U.S. Provisional Application No. 62/363,284, filed Jul. 17, 2016, the entire content of which is incorporated by reference herein.

BACKGROUND OF THE INVENTION

*Plectranthus amboinicus* (also known previously or alternatively as *Coleus amboinicus* Lour., *Coleus aromaticus* Benth., *Coleus aromaticus* auct., *Plectranthus aromaticus* Roxb., *Plectranthus aromaticus* Benth., and *Plectranthus amboinicus* (Lour.) Spreng.), is a perennial medicinal herb of the Lamiaceae (also known as Labiatae) family native to Southern and Eastern Africa. *Plectranthus amboinicus* is also known as patchouli, Cuban oregano, Indian borage, Indian mint, Mexican mint, Mexican oregano, country borage, and Spanish thyme.

*Centella asiatica* (also known previously or alternatively as *Centella asiatica* Urban, *Centella asiatica* (L.) Urban, *Hydrocotyle asiatica* L., and *Trisanthus cochinchinensis* Lour.) is a perennial medicinal plant of the family Mackinlayaceae or subfamily Mackinlayoideae of the Apiaceae (also known as Umbelliferae) family native to Asia, Africa, and South America. *Centella asiatica* is also known as European water-marvel, gotu kola, Kola, pennywort, Indian pennywort, marsh pennywort, pennyweed, Indian *ginseng*, Horse-hoof grass, Pegaga, Mandookaparni, Tiger herbal, Spadeleaf, or Tono. Extracts of *Centella asiatica* generally comprise two major compounds: asiaticoside and madecassic acid.

SUMMARY OF THE INVENTION

The present disclosure is based, at least in part, on the superior therapeutic effects of a topical formulation comprising a combination of a *Plectranthus amboinicus* extract and a *Centella asiatica* extract as described herein, which comprise salvigenin and/or asiaticoside, in promoting wound healing in, e.g., diabetic patients having diabetic foot ulcer. For example, the topical formulation successfully enhanced healing of foot ulcer in diabetic patients and the efficacy was much higher than Aquacel®, a positive control. Local application of the topical formulation also showed limited systemic distribution of at least the active ingredients therein (salvigenin and/or asiaticoside) in DFU patients, and was found safe in the patients.

Accordingly, provided herein is a topical formulation, comprising: (i) an active agent comprising salvigenin in an amount of about 0.0001% to 0.5% (w/w) (e.g., about 0.0001% to 0.1% by weight) and asiaticoside in an amount of about 0.05% to 5% (w/w) (e.g., about 0.05% to 1% by weight); (ii) a viscosity increasing agent in an amount of about 1.0-10% (w/w); (iii) an ointment base in an amount of about 5-30% (w/w); (iv) an antimicrobial preservative in an amount of about 0.005-0.2% (w/w); and (v) an emulsifying agent in an amount of about 0.5-10% (w/w).

In some embodiments, the active agent is a *Plectranthus amboinicus* (PA) extract, a *Centella asiatica* extract (CA), or a combination of the PA and CA extracts, which (individually or in combination) comprises salvigenin and asiaticoside.

In one embodiment, the active agent is a combination of the *Plectranthus amboinicus* extract and the *Centella asiatica* extract. The active agent may be about 0.1-30% (w/w) and comprise at least salvigenin and asiaticoside. In some instances, the topical formulation may comprise salvigenin ranging from about 0.0001% to 0.5% (w/w), for example, about 0.0001% to 0.1% (w/w). In some instances, the topical formulation may comprise salvigenin ranging from about 0.0001% to 0.1% (w/w) and asiaticoside ranging from 0.05% to 1% (w/w). In any of the topical formulations described herein, the active agent therein may further comprise cirsimaritin, madecassoside, or a combination thereof.

The *Plectranthus amboinicus* extract may be about 0.1-5% (w/w) or about 0.1-1% (w/w) in the topical formulation. In some embodiments, the *Plectranthus amboinicus* extract comprises flavonoids, essential oils, phenolics, terpenoids, or a combination thereof.

The *Plectranthus amboinicus* extract may be prepared by contacting a whole *Plectranthus amboinicus* or a part thereof with a solvent having a polarity index lower than 7 (e.g., less than 5) to produce a solution and drying the solution to produce the *Plectranthus amboinicus* extract. In a specific embodiment, the *Plectranthus amboinicus* extract is prepared by a process comprising: (i) contacting a whole *Plectranthus amboinicus* or a part thereof with an alcohol (e.g., ethanol) to produce a crude *Plectranthus amboinicus* extract; (ii) contacting the crude extract with a non-ionic adsorbent resin; (iii) eluting the non-ionic adsorbent resin with a solvent having a polarity index less than 7 (e.g., less than 5) to produce a solution; and (iv) drying the solution to produce the *Plectranthus amboinicus* extract.

Alternatively or in addition, the *Centella asiatica* extract may comprise asiaticoside, madecassoside, or both. In some embodiments, the *Centella asiatica* extract is about 0.1-20% (w/w) or about 0.5-5% (w/w) in the topical formulation.

In some embodiments, the ratio between the *Plectranthus amboinicus* extract and the *Centella asiatica* extract is about 1:10 to about 10:1, for example, about 1:5 to 5:1.

The topical formulation may comprise the viscosity increasing agent at about 1.0-10% (w/w). Examples of the viscosity increasing agents include, but are not limited to, cetostearyl alcohol, cholesterol, stearyl alcohol, chlorocresol, white wax, stearic acid, cetyl alcohol, or a combination thereof.

The topical formulation may comprise the ointment base at about 5-30% (w/w) (e.g., 10-30% by weight). In some instances, the ointment base can be a cream basis. Examples of the ointment base include, but are not limited to, one or more petrolatum compounds (e.g., liquid petrolatum, white petrolatum).

The antimicrobial preservative in the topical formulation described herein can be about 0.005-0.2% (w/w) (e.g., 0.01-0.2% by weight). It may comprise one or more paraben compounds (e.g., methyl paraben and/or propyl paraben).

The emulsifying agent (e.g., Span® 60 and/or Tween® 60) in the topical formulation may be about 0.5-10% (w/w) (e.g., 0.5-6% by weight).

In some examples, the topical formulation described herein may comprise the ointment base at about 10-30% (w/w), the antimicrobial preservative at about 0.01-0.2% (w/w), and the emulsifying agent at about 0.5-6% (w/w).

Any of the topical formulations described herein may optionally further comprise one or more solvents, for example, propylene glycol.

In one example, the topical formulation described herein comprises a combination of the *Plectranthus amboinicus* extract and the *Centella asiatica* extract in an amount of about 0.1-30% (w/w), cetostearyl alcohol in an amount of about 1.0-10% (w/w) (e.g., about 2 to 8% or about 3-7%), a combination of white petrolatum and liquid petrolatum in a total amount of about 5-30% (w/w) (e.g., about 5-25% or about 5-20%), a combination of methyl paraben and propyl paraben in a total amount of about 0.005-0.2% (w/w), and a combination of sorbitan monostearate and polysorbate 60 in a total amount of about 0.5-10% (w/w) (e.g., 0.5-8% or 0.5-6%). Such a topical formulation may further comprise propylene glycol in an amount of about 2-20% (w/w) (e.g., 2-10% or 4-15%).

In another aspect, the instant disclosure provides a method for wound healing, comprising administering the topical formulation disclosed herein to a wound site of a subject in need thereof. In one embodiment, the topical formulation can be administered at least once per day, for example, twice daily.

In one example, the subject to be treated can be a human diabetic patient suffering from diabetic foot ulcer. For example, the human diabetic patient may have type I or type II diabetes. In another example, the subject is a human patient having an open wound, for example, abrasion, incision, laceration, puncture, or avulsion. In another example, the subject is a human patient having a chronic wound, which may be a surgical wound, a traumatic wound, a pressure ulcer, a venous ulcer, a diabetic ulcer, or a wound caused by a carcinoma, burn, atopic dermatitis, bedsore. In some examples, the subject is a human patient having acne.

Also within the scope of the present disclosure are (i) a topical formulation as described herein for use in promoting wound healing, and (ii) uses of the *Plectranthus amboinicus* extract, the *Centella asiatica* extract, or a combination thereof in manufacturing a medicament for use in promoting wound healing, wherein the *Plectranthus amboinicus* extract, the *Centella asiatica* extract, or the combination thereof is formulated into a topical formulation as described herein.

The details of one or more embodiments of the invention are set forth in the description below. Other features or advantages of the present invention will be apparent from the following drawings and detailed description of several embodiments, and also from the appended claims.

DETAILED DESCRIPTION OF THE INVENTION

Foot ulcers are a common complication associated with diabetes as a result of skin tissue breaking down and exposing the underneath layers. All diabetics are at risk for developing foot ulcers. About 15-20% of diabetics would develop foot ulcers. Among them, approximate 33% of the patients would require amputation.

Currently available treatments for diabetic foot ulcers (DFUs) include wearing protective instruments, such as diabetic shoes, casts, food braces, compression wraps, and shoe inserts to prevent corns and calluses. Such medical instruments could be costly and often cause inconvenience in patients' daily life. Alternatively, surgical procedures may be performed to remove foot ulcers with a debridement. To date, Regranex® is the only medication approved by the Food and Drug Administration (FDA) for treating DFU. In June 2008, the FDA announced a new labeling change of Regranex® to indicate that there was a five-fold increased risk of cancer mortality in the group exposed to Regranex®.

The present disclose is based, at least in part, on the development of a topical formulation comprising a combination of a *Plectranthus amboinicus* extract and a *Centella asiatica* extract, which showed significantly higher efficacy in promoting wound healing and low side effects in DFU patients. This topical formulation is cream-based and comprises at least about 0.0001% to 0.5% (w/w) salvigenin as an active ingredient. In some embodiments, the topical formulation may further comprise about 0.05% to 5% (w/w) asiaticoside as an additional active ingredient. The topical formulation further comprises about 1.0-10% (w/w) viscosity increasing agent(s), about 5-30% (w/w) ointment base(s) (e.g., cream base), about 0.005-0.2% (w/w) antimicrobial preservative(s); and about 0.5-10% (w/w) emulsifying agent(s). All of the components may be dissolved in one or more suitable solvents such as propylene glycol and water.

Pharmacokinetic studies of the topical cream formulation noted above showed its safety in DFU patients. More importantly, topical administration of the cream formulation led to very low systemic distribution of at least the two active ingredients, salvigenin and asiaticoside, after local application to wound sites of the patients, and was found to be safe in the patients being treated with the topical formulation locally.

Further, a Phase III clinical trial was conducted to evaluate the efficacy of the cream-based topical formulation for treating chronic diabetic foot ulcer. Unexpectedly, the topical ointment showed significantly higher efficacy in promoting ulcer closure in diabetic patients, particularly in those having large ulcers or plantar ulcers; as compared with a control product, Aquacel®.

Accordingly, provided herein are topical formulations that comprise one or both of the *Plectranthus amboinicus* extract and the *Centella asiatica* extract, and methods of using such for promoting wound healing in a subject in need of the treatment.

Topical Formulations

The instant disclosure herein provides a topical formulation for promoting wound healing (e.g., the healing of wounds for diabetic patients), comprising an active agent, which can be a *Plectranthus amboinicus* extract that comprises salvigenin, a *Centella asiatica* extract that comprises asiaticoside, or a combination of the *Plectranthus amboinicus* extract and the *Centella asiatica* extract. The topical formulation described herein may comprises salvigenin in an amount ranging from about 0.0001% to about 0.5%

(w/w), and optionally asiaticoside, which may be in an amount ranging from about 0.05% to about 5% (w/w). In some embodiments, the topical formulation comprises the *Plectranthus amboinicus* extract, the *Centella asiatica* extract, or both in an amount of about 0.1-30% (w/w).

The topical formulation further comprises one or more carriers or excipients, including one or more of viscosity increasing agents (e.g., about 1.0-10%), one or more ointment bases (e.g., one or more cream base) which may range from about 5-30%, one or more antimicrobial preservative (e.g., about 0.005-0.2% by weight), one or more emulsifying agents (about 0.5-10% by weight) or a combination thereof. These components may be dissolved or disbursed in a suitable solvent.

(i) Active Agents

The active agent in the topical formulation described herein comprises salvigenin and optionally asiaticoside. In some embodiments, the active agent can be either a *Plectranthus amboinicus* extract that comprises salvigenin or a *Centella asiatica* extract that comprises asiaticoside alone, or a combination thereof. The concentration of the active agent in the topical formulation may range from about 0.1-30% (w/w). For example, the active agent may comprise about 0.1-5%, 0.5-3%, 1-2%, 1-3%, 2-10%, 5-10%, 5-15%, 10-15%, 15-20%, 10-20%, 20-25%, 15-30%, 20-30%, 10-30%, or 25-30% (w/w) of the topical formulation. The concentration of the active agent in the topical formulation described herein refers to the percentage of the total weight of the active agent in dry form of the total weight of the topical formulation as a whole.

The topical formulation described herein may comprise about 0.0001% to 0.5% (w/w) salvigenin, for example, about 0.001% to 0.5% (w/w), about 0.001% to 0.3% (w/w), about 0.001% to 0.2% (w/w), about 0.01% to 0.1% (w/w), about 0.002% to 0.5% (w/w), about 0.002% to 0.4% (w/w), about 0.002% to 0.3% (w/w), about 0.001% to 0.1% (w/w), about 0.005% to 0.01% (w/w), about 0.01% to 0.5% (w/w), about 0.02% to 0.5% (w/w), and about 0.1% to 0.5% (w/w). Alternatively or in addition, the topical formulation described herein may comprise asiaticoside in an amount ranging from about 0.05% to about 5% (w/w), e.g., about 0.1-2.5% (w/w), about 0.1-2% (w/w), about 0.1 to 1% (w/w), about 0.25-2.5% (w/w), about 0.5-5% (w/w), about 0.5-2.5% (w/w), or about 0.5-1% (w/w).

As used herein, the term "about" intends to a strict numerical boundary to the specified parameters (including both the upper and lower limits). A skilled person in the art would have understood the meaning of "about" in association with a specific context. In some instances, the term "about" refers to a particular value +/−5% (e.g., +/−3% or +/−2%).

In one embodiment, the active agent in the topical formulation is a combination of the *Plectranthus amboinicus* extract that comprises salvigenin and the *Centella asiatica* extract that comprises asiaticoside. The ratio between the *Plectranthus amboinicus* extract and the *Centella asiatica* extract may be about 1:10 to 10:1. For example, the ratio between the *Plectranthus amboinicus* extract and the *Centella asiatica* extract in the topical formulation may be about 1:10 to 1:1, about 1:1 to 10:1, about 1:10 to 1:5, about 1:5 to 1:1, about 10:1 to 5:1, about 5:1 to 1:1, about 1:10 to 1:4, about 1:4 to 1:1, about 10:1 to 4:1, or about 4:1 to 1:1.

A *Plectranthus amboinicus* extract refers to an extract obtained from *Plectranthus amboinicus* plant using one or more suitable solvents. In some instances, at least one of the solvents used for preparing the extract has a polarity index lower than 7 (e.g., less than 5). See Table 1 below. As used herein, a solvent refers to a substance or a mixture of substances that dissolves another to form a solution. A *Plectranthus amboinicus* extract as described herein may be prepared using one solvent. The solvent used in each extracting step for preparing the extracts described herein (including both *Plectranthus amboinicus* and *Centella asiatica* extracts) may be a single solvent. Alternatively, it can be a mixture of two or more solvents.

The *Plectranthus amboinicus* extract described herein may comprise terpenoids (e.g., monoterpenoids, diterpenoids, triterpenoids, and/or sesquiterpenoids), flavonoids, phenolics, essential oils, or a combination thereof. The *Plectranthus amboinicus* extract may be present in the topical formation at a concentration of about 0.1-5% (w/w). For example, the topical formulation may comprise about 0.1-0.5%, 0.5-1%, 1-1.5%, 1.5-2%, 2-2.5%, 2.5-3%, 3-3.5%, 3.5-4%, 4-4.5%, or 4.5-5% (w/w) of the *Plectranthus amboinicus* extract. Alternatively, the topical formulation may comprise about 0.1-1%, 0.1-2%, 0.1-3%, 0.1-4%, or 0.1-5% percent (w/w) of the *Plectranthus amboinicus* extract. In a specific embodiment, the topical formulation comprises about 0.1-1% or 0.1-0.5% of the *Plectranthus amboinicus* extract.

The *Plectranthus amboinicus* extract described herein may be prepared by extracting a whole *Plectranthus amboinicus* plant or a part thereof with one or more suitable solvents to produce a solution and then drying the solution to produce the *Plectranthus amboinicus* extract. Since the *Plectranthus amboinicus* extract comprises flavonoids, terpenoids (e.g., monoterpenoids, diterpenoids, triterpenoids, and/or sesquiterpenoids), phenolics, or essential oils, which are non-polar molecules, at least one of the extracting solvents may have a relatively low polarity (e.g., having a polarity index lower than 7) to facilitate dissolution of the non-polar molecules. "Extracting" can be performed by either contacting the *Plectranthus amboinicus* material directly with a suitable solvent or by eluting active components of *Plectranthus amboinicus* from resins on which the active components are attached.

Table 1 below lists commonly used solvents and their polarity index (Snyder polarity index):

TABLE 1

Exemplary Solvents and Their Polarity Index

| Solvent | Polarity Index (Snyder) |
|---|---|
| cyclohexane | 0 |
| n-hexane | 0 |
| n-decane | 0.3 |
| i-octane | 0.4 |
| octane | 0.4 |
| butyl ether | 1.7 |
| carbon tetrachloride | 1.7 |
| triethyl amine | 1.8 |
| i-propyl ether | 2.2 |
| toluene | 2.3 |
| xylene, p- | 2.4 |
| t-butyl methyl ether | 2.9 |
| benzene | 3 |
| benzyl ether | 3.3 |
| dichloromethane | 3.4 |
| methylene chloride | 3.4 |
| chloroform | 3.4-4.4 |
| dichloroethane | 3.7 |
| ethylene dichloride | 3.7 |
| butanol, 1- | 3.9 |
| i-butyl alcohol | 3.9 |
| tetrahydrofuran | 4.2 |
| ethyl acetate | 4.3 |

TABLE 1-continued

Exemplary Solvents and Their Polarity Index

| Solvent | Polarity Index (Snyder) |
|---|---|
| propanol, 1- | 4.3 |
| propanol, 2- | 4.3 |
| methyl acetate | 4.4 |
| cyclohexanone | 4.5 |
| methyl ethyl ketone (MEK) | 4.5 |
| nitrobenzene | 4.5 |
| benzonitrile | 4.6 |
| dioxane, 1,4- | 4.8 |
| dioxane, p | 4.8 |
| ethanol | 5.2 |
| nitroethane | 5.3 |
| pyridine | 5.3 |
| acetone | 5.4 |
| benzyl alcohol | 5.5 |
| methoxyethanol, 2- | 5.7 |
| acetic acid | 6.2 |
| acetonitrile | 6.2 |
| dimethyl formamide, N,N- | 6.4 |
| dimethyl sulfoxide | 6.5 |
| methanol | 6.6 |
| formamide | 7.3 |
| water | 9 |

In some examples, a solvent having a polarity index lower than 7 can be used for extracting the active components from *Plectranthus amboinicus* to produce the *Plectranthus amboinicus* extract. Such a solvent can be ethyl acetate, methyl acetate, propanol, butanol, or chloroform. Alternatively, the solvent can be a mixture of one or more solvents having different polarity index. Examples include, but are not limited to, a mixture of ethanol and ethyl acetate, ethyl acetate and butanol, ethanol and propanol, methyl acetate and butanol.

In some embodiments, the *Plectranthus amboinicus* extract may be prepared by a process involving the use of one solvent, such as a solvent having a polarity index lower than 7 (e.g., <about 6.5, <about 6.0; <about 5.5, <about 5.0, <4.9, <4.8, <4.7, <4.6, or <4.5). Examples include, but are not limited to, methanol, ethanol, acetone, ethyl acetate, butanol, dichloromethane, or a combination thereof.

An exemplary process for preparing the *Plectranthus amboinicus* extract is provided below. See also FIG. 1.

Figure 1:
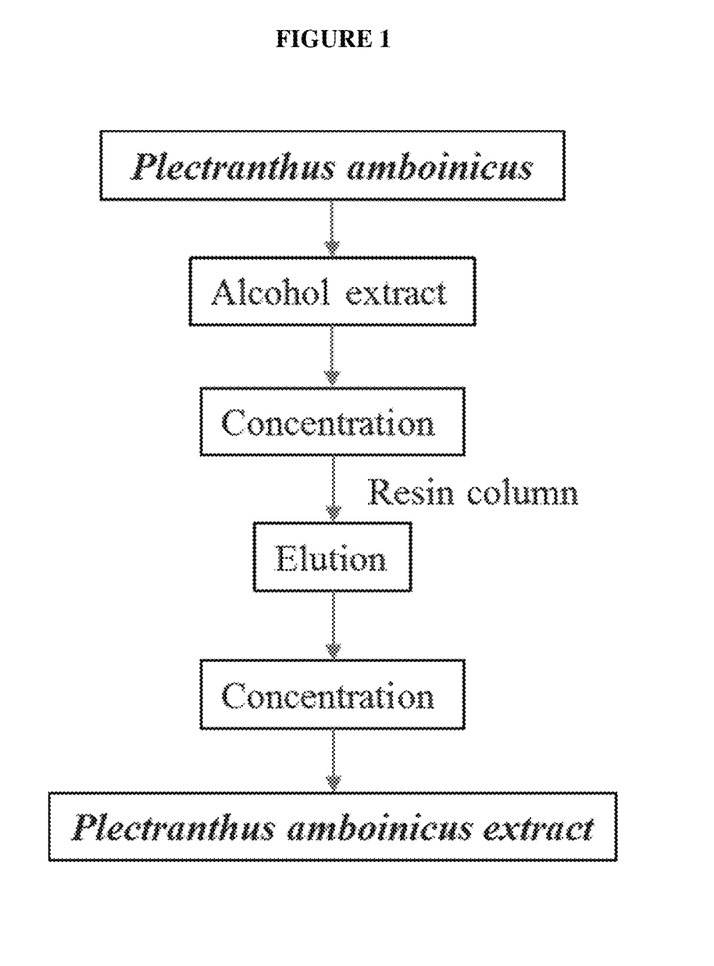
FIG. 1 is a flowchart showing an exemplary process for preparing *Plectranthus amboinicus* extracts.

*Plectranthus amboinicus* materials, which can be a whole *Plectranthus amboinicus* or a part thereof (e.g., leaves), can be prepared by routine methodology. The *Plectranthus amboinicus* material can be a fresh plant or a part thereof. Alternatively, the *Plectranthus amboinicus* material can be in dried form. The *Plectranthus amboinicus* can optionally be dried to form powders, which can be used as the *Plectranthus amboinicus* material for preparing the *Plectranthus amboinicus* extract.

Any of the *Plectranthus amboinicus* materials as described herein can be extracted, one or more times, by a suitable solvent to produce a crude extract. The solvent for use in preparing the crude extract may be a high-polarity solvent, for example, having a polarity index above 5 and preferably below 7 (e.g., >5.2; >5.5, >5.8, >6 or above and preferably below 7). Examples include, but are not limited to, ethanol, acetone, methanol, water, or a combination thereof. If necessary, the crude extract can be concentrated by a conventional method to produce a concentrated crude extract.

The crude extract can then be brought in contact with a suitable resin (e.g., a non-ionic absorbent resin) under suitable conditions that allow for binding of active components in the crude extract onto the resin. Exemplary resins for use in preparing the *Plectranthus amboinicus* extract include, but are not limited to, DIAION® HP20, DIAION® HP20SS, Sepabeads® SP207, Amberlite™ XAD-2, or Amberlite™ XAD-4.

Afterwards, the resin can be washed one or more times and eluted with a suitable solvent, for example, a solvent having a polarity index lower than 7, to produce a *Plectranthus amboinicus* extract, which can then be dried by a conventional method (e.g., freeze-drying, spray-drying, or concentration drying) to produce dried the *Plectranthus amboinicus* extract, which can be in semisolid or paste form.

In some embodiments, the resin absorption step can be performed by mixing the crude extract with the resin in a container. In other embodiments, the resin separation step can be performed by a chromatography column setting.

The *Centella asiatica* extract as described herein refers to an extract obtained from whole *Centella asiatica* plants or a part thereof. The *Centella asiatica* extract may comprise asiaticoside, madecassic acid, or a combination thereof.

The *Centella asiatica* extract may be present in the topical formation at a concentration of about 0.1-20% (w/w). For example, the topical formulation may comprise about 0.1-0.5%, 0.5-1%, 1-1.5%, 1.5-2%, 2-2.5%, 2.5-3%, 3-3.5%, 3.5-4%, 4-4.5%, 4.5-5%, 5-5.5%, 5.5-6%, 6-6.5%, 6.5-7%, 7-7.5%, 7.5-8%, 8-8.5%, 8.5-9%, 9-9.5%, 9.5-10%, 10-10.5%, 10.5-11%, 11-11.5%, 11.5-12%, 12-12.5%, 12.5-13%, 13-13.5%, 13.5-14%, 14-14.5%, 14.5-15%, 15-15.5%, 15.5-16%, 16-16.5%, 16.5-17%, 17-17.5%, 17.5-18%, 18-18.5%, 18.5-19%, 19-19.5%, or 19.5-20% (w/w) of the *Centella asiatica* extract. Alternatively, the topical formulation may comprise about 0.1-5%, 0.1-10%, 0.1-15%, 0.1-20%, 0.5-5%, 0.5-10%, 0.5-15%, or 0.5-20% (w/w) of the *Centella asiatica* extract. In specific examples, the topical formulation may comprise about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20 percent (w/w) of the *Centella asiatica* extract.

The *Centella asiatica* extract can be prepared following a conventional method, for example, those described in U.S. Pat. Nos. 5,834,437, 6,417,349, 6,475,536, and 6,267,996, CN 1313124, CN 1089497, and CN 1194154. Below is an example.

Figure 2:
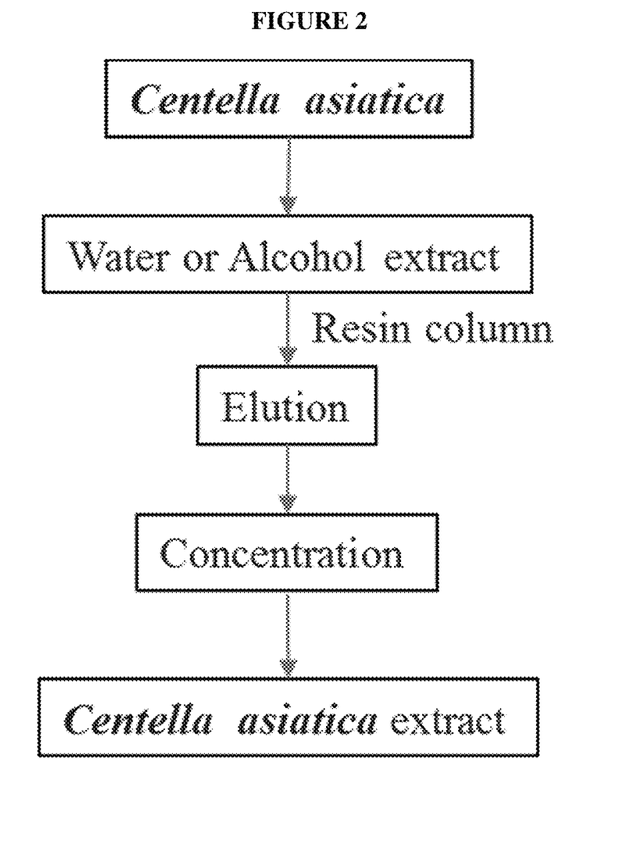
FIG. 2 is a flowchart showing an exemplary process for preparing *Centella asiatica* extracts.

*Centella asiatica* materials can be prepared via routine practice. Such materials can be fresh *Centella asiatica* plant or a part thereof, or dried *Centella asiatica*. The *Centella asiatica* materials can be extracted with a suitable solvent such as water, ethanol, or a mixture thereof, to produce a crude extract. The crude extract, which can be optionally concentrated, can be either mixed with a suitable resin or loaded onto a column packed with the resin. After being washed for one or more times, the resin can be eluted with a suitable solvent. The resultant eluent can be concentrated to form a paste, which can be dried by a conventional method, for example, vacuum dry, to produce powders of the *Centella asiatica* extract. When necessary, the *Centella asiatica* powder can be grinded through a mesh (e.g., a No. 100 mesh). See also FIG. 2.

In one example, an extract of *Plectranthus Amboinicus* can be prepared as follows. An overground part of *Plectranthus Amboinicus* (about 1.5 g), including leaves and/or stems, can be collected and extracted with a solvent having a polarity less than 7 (e.g., methanol, ethanol, acetone, ethyl acetate, butanol, dichloromethane, or a combination thereof) at room temperature for 30 min to 6 hours. Alternatively, this extraction process can be carried out at a temperature of about 50 to 80° C. The resultant crude extract can be directly loaded to a non-ionic adsorbent resin column and eluted by a solvent having a polarity less than 6 (e.g., ethanol, ethyl acetate, butanol, dichloromethane, hexane, toluene, or a combination thereof). The eluted components can be collected and purified by extraction with a solvent having a polarity less than 6 (e.g., those described herein). The resultant filtrate can be collected to produce a PA extract.

An extract of *Centella Asiatica* can be prepared by the same or similar process as described above. The PA Extract and/or CA Extract may be concentrated using a pressure-reducing rotary evaporator.

(ii) Carriers and Excipients

The topical formulation further comprises one or more carriers and excipients, including viscosity increasing agents, ointment bases (e.g., cream bases), antimicrobial preservatives, emulsifying agents, and/or solvents.

A "viscosity increasing agent" is an agent that is used to thicken a formulation. Exemplary viscosity increasing agents may include, for example, cetostearyl alcohol, cholesterol, stearyl alcohol, chlorocresol, white wax, stearic acid, cetyl alcohol, or a combination thereof. The viscosity increasing agent may be present in the topical formation at a concentration of about 1.0-10% (w/w). For example, the topical formulation may comprise about 1-1.5%, 1.5-2%, 2-2.5%, 2.5-3%, 3-3.5%, 3.5-4%, 4-4.5%, 4.5-5%, 5-5.5%, 5.5-6%, 6-6.5%, 6.5-7%, 7-7.5%, 7.5-8%, 8-8.5%, 8.5-9%, 9-9.5%, or 9.5-10% (w/w) of the viscosity increasing agent. Alternatively, the topical formulation may comprise about 1-5%, 2.5-7.5%, or 5-10% (w/w) of the viscosity increasing agent.

An "ointment base" can be any semisolid preparation or vehicle into which an active agent may be incorporated. Exemplary ointment bases include, but are not limited to, oleaginous ointment bases (e.g., white petrolatum or white ointment), absorption ointment bases (e.g., hydrophilic petrolatum, anhydrous lanolin, Aquabase™, Aquaphor®, and Polysorb®), water/oil emulsion ointment bases (e.g., cold cream, hydrous lanolin, rose water ointment, Hydrocream™, Eucerin®, and Nivea®), oil/water emulsion ointment bases (e.g., hydrophilic ointments, Dermabase™, Velvachol®, and Unibase®), and water-miscible ointment bases (e.g., polyethylene glycol (PEG) ointment and Polybase™). Ointment bases may be pharmacologically inert but can entrap water in order to provide an emollient protective film. In a specific embodiment, the ointment base may be any petrolatum compound (e.g., petrolatum, white petrolatum, white soft paraffin, liquid petrolatum, liquid paraffin). In a further specific embodiment, the ointment base is white petrolatum (CAS number 8009-03-8). The ointment base may be present in the topical formation at a concentration of about 5-30% (w/w), e.g., 10-30% (w/w). For example, the topical formulation may comprise about 5-25%, 5-20%, 5-15%, 5-15%, 10-15%, 15-20%, 20-25%, or 25-30% (w/w) of the ointment base. Specifically, the topical formulation may comprise about 5, 6, 7, 8, 9, 10, 11, 12, 13, 14, 15, 16, 17, 18, 19, 20, 21, 22, 23, 24, 25, 26, 27, 28, 29, or 30 percent (w/w) of the ointment base.

In some embodiments, the "ointment base" described herein contains less than 20% water and volatiles, and more than 50% hydrocarbons, waxes, or polyols as the vehicle.

In some embodiments, the "ointment base" described herein is a "cream base," which contains more than 20% water and volatiles and/or typically contain less than 50% hydrocarbons, waxes, or polyols as the vehicle for the drug substance. The cream base can be a multiphase preparation containing a lipophilic phase and an aqueous phase. In some instances, the cream base is a lipophilic cream base, which has a lipophilic phase as the continuous phase. Such a cream base usually contains water-in-oil emulsifying agents such as wool alcohols, sorbitan esters and monoglycerides. In other instances, the cream base is a hydrophilic cream base, which has an aqueous phase as the continuous phase. Such a cream base typically contains oil-in-water emulsifying agents such as sodium or trolamine soaps, sulfated fatty alcohols, polysorbates and polyoxyl fatty acid and fatty alcohol esters, which may be in combination with water-in-oil emulsifying agents, if needed.

An "antimicrobial preservative" can be any compound capable of destroying microbes, prevent the multiplication or growth of microbes, or prevent the pathogenic action of microbes. Exemplary antimicrobial preservatives include, but are not limited to, a paraben compound (an ester of para-hydroxybenzoic acid; e.g., paraben, methylparaben, ethylparaben, propylparaben, butylparaben, heptylparaben, benzylparaben, isobutylparaben, isopropylparaben, benzylparaben, or their sodium salts), benzalkonium chloride, benzethonium chloride, benzyl alcohol, boric acid, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. The antimicrobial preservative may be present in the topical formation at a concentration of about 0.005-0.2%, e.g., about 0.01-0.2% (w/w). For example, the topical formulation may comprise about 0.005-0.01%, 0.01-0.05%, 0.05-0.1%, 0.1-0.15%, or 0.15-0.2% (w/w) of the antimicrobial preservative. Specifically, the topical formulation may comprise about 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or 0.2 percent (w/w) of the antimicrobial preservative.

An "emulsifying agent" is a compound or substance which acts as a stabilizer for a mixture of two or more liquids that are normally immiscible (unmixable or unblendable). Exemplary emulsifying agents may include, but are not limited to, natural emulsifying agents (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and Veegum [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, propylene glycol monostearate, and polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, and methylcellulose), sorbitan fatty acid esters (e.g., polyoxyethylene sorbitan monolaurate [Tween® 20], polyoxyethylene sorbitan [Tween® 60], polyoxyethylene sorbitan monooleate [Tween® 80], sorbitan monopalmitate [Span® 40], sorbitan monostearate [Span® 60], sorbitan tristearate [Span® 65], glyceryl monooleate, and sorbitan monooleate [Span® 80]), polyoxyethylene esters (e.g., polyoxyethylene monostearate [Myrj® 45], polyoxyethylene hydrogenated castor oil, polyethoxylated castor oil, polyoxymethylene stearate, and Solutol), sucrose fatty acid esters, polyethylene glycol fatty acid esters (e.g., Cremophor®), polyoxyethylene ethers (e.g., polyoxyethylene lauryl ether [Brij® 30]), and poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, and docusate sodium, and/or combinations thereof. The emulsifying agent may be present in the topical formation at a concentration of about 0.5-10% (w/w), e.g., 0.5-6% (w/w). For example, the topical formulation may comprise about 0.5-1%, 1-1.5%, 1.5-2%, 2-2.5%, 2.5-3%, 3-3.5%, 3.5-4%, 4-4.5%, 4.5-5%, 5-5.5%, 5.5-6%, 5-10%, 6-10%, or 8-10% (w/w) of the emulsifying agent. Specifically, the topical formulation may comprise about 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 percent (w/w) of the emulsifying agent.

The topical formulation of the invention may further contain one or more solvents (e.g., non-water solvents or water). Exemplary non-water solvents may include, but are not limited to, any known solvent including propylene glycol, glycol, and mixtures thereof. The non-water solvent may be present in the topical formation at a concentration of about 2-65% (w/w). For example, the topical formulation may comprise about 2-15%, 15-30%, 30-45%, or 45-65% (w/w) of the solvent. In some embodiments, the topical formulation of the invention may also contain water.

In some embodiments, the topical formulation of the invention may further comprise one or more emollients, fragrances, or pigments. The topical formula may also be used in conjunction with a wound dressing (e.g., bandage with adhesive, plaster patch and the like). (e.g., cyclohexane, n-hexane, n-decane, i-octane, octane, butyl ether, carbon tetrachloride, triethyl amine, i-propyl ether, toluene, p-xylene, t-butyl methyl ether, benzene, benzyl ether, dichloromethane, methylene chloride, chloroform, dichloroethane, ethylene dichloride, 1-butanol, i-butyl alcohol, tetrahydrofuran, ethyl acetate, 1-propanol, 2-propanol, methyl acetate, cyclohexanone, methyl ethyl ketone (MEK), nitrobenzene, benzonitrile, 1,4-dioxane, or p-dioxane).

Methods for Promoting Wound Healing

Any of the topical formulations described herein can be used for promoting wound healing in a subject in need of the treatment. The topical formulation may be applied to a wound site following a suitable dosage and treatment regimen. The dosage and administration regimen for the described method will depend on the nature and condition of the wound being treated, the age and condition of the patient, and any prior or concurrent therapy. In some instances, the topical formulation can be applied once every week, once every other day, once daily, twice daily, three times daily, or four time daily for a suitable period of time. The treatment may be terminated when the wound is recovered. When necessary, the treatment may resume, for example, if a wound recurs.

The term "wound" refers to an injury to living tissue caused by a cut, blow, or other impact (e.g., caused by a medical condition such as a skin disorder), typically one in which the skin is cut or broken. Wound may be associated with a medical condition, for example, a skin disorder. The term "wound healing" denotes the dynamic and complex process of replacing devitalized or missing cellular structures and/or tissue layers. The term "promotion of wound healing" or "promoting wound healing" denotes the inducement of an increased level or rate of replacement for devitalized or missing cellular structures and/or tissue layers. As an example, promotion of wound healing may be indicated by partial or complete ulcer closure or an increase in the healing rate of an ulcer (including but not limited to more rapid changes in ulcer size, area, or severity, a more rapid closure of the ulcer, and/or an increase in the percentage change from baseline in ulcer size, area, or severity when compared to a control ulcer treated with a placebo).

The subject to be treated by the topical formulation can be a human or a non-human mammal. In some embodiments, the subject is a human patient having an open wound, which refers to an injury or damage to living tissues (e.g., skin) that cause a disruption in the normal continuity of biological structures. An open wound may include, but is not limited to, an abrasion, incision, laceration, puncture, avulsion, cut, or other similar injuries.

In other embodiments, the subject is a human patient having a chronic wound, which can be injuries or damage to living tissues (e.g., skin) that cause a disruption in the normal continuity of biological structures and do not heal in an orderly set of stages and/or in a predictable amount of time. A chronic wound may include, but is not limited to: a surgical wound, a traumatic wound, a pressure ulcer, a venous ulcer, or a diabetic ulcer. In other examples, a chronic wound may be associated with a disease or disorder, for example, a carcinoma, burn, bedsore, a skin disorder such as atopic dermatitis.

In one example, the subject is a human patient having foot ulcer associated with diabetes (e.g., type I or type II). Diabetes mellitus (also known as diabetes) is a group of metabolic diseases which result in high blood sugar levels over a prolonged period. Diabetes may result from the pancreas not producing enough insulin or the cells of the body not responding properly to the insulin produced. The three main types of diabetes mellitus are Type I (also known as "insulin-dependent diabetes mellitus" (IDDM) or "juvenile diabetes"; results from the failure of the pancreas to produce enough insulin), Type 2 (also known as "non-insulin-dependent diabetes mellitus" (NIDDM) or "adult-onset diabetes"; results from the failure of cells to respond to insulin properly), and gestational diabetes (seen during pregnancy when high blood sugar levels are observed in the absence of a previous history of diabetes). Many serious complications are observed in diabetic patients including, but not limited to, chronic wounds such as diabetic foot ulcers (also known as diabetic ulcers).

In some embodiments, the subject to be treated by the methods described herein suffers from a severe wound, for example, having an ulcer with an area greater than 2 $cm^2$ (e.g., 3 $cm^2$, 4 $cm^2$ or 5 $cm^2$). In some examples, the subject suffers from one or more plantar ulcers Kits for Use in Promoting Wound Healing The present disclosure also provides kits for use in promoting wound healing. Such kits may include one or more containers comprising a topical formulation as described herein, which comprises a *Plectranthus amboinicus* extract, a *Centella asiatica* extract, or a combination of the *Plectranthus amboinicus* extract and the *Centella asiatica* extract.

In some embodiments, the kit may comprise instructions for use in accordance with any of the methods described herein. The included instructions may comprise a description of administration of the topical formulation to promote wound healing according to any of the methods described herein. The kit may further comprise a description of selecting an individual suitable for treatment based on identifying whether that individual has wounds in need of treatment.

The instructions relating to the use of a topical formulation generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for promoting wound healing. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. At least one active agent in the composition is an active agent selected from the group consisting of a *Plectranthus amboinicus* extract, a *Centella asiatica* extract, and a combination of a *Plectranthus amboinicus* extract and a *Centella asiatica* extract.

Kits may optionally provide additional components such as interpretive information. Normally, the kit comprises a container and a label or package insert(s) on or associated with the container. In some embodiments, the invention provides articles of manufacture comprising contents of the kits described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Effects of *Plectranthus amboinicus* Extract and *Centella asiatica* Extract on Endothelial Cell Proliferation and Migration (i) MTT Assay—Proliferation The *Plectranthus Amboinicus* (PA) Extract and *Centella Asiatica* (CA) Extract were prepared following the descriptions provided herein. The EA.hy926 endothelial cell line was used for this study. The cells were plated at a density of $4\times10^4$ cells/well in a 96-well plate for one day and then treated with the PA or CA extract in a serum-free medium for 70 hour. After the treatment, the cells were stained with MTT dye for 2 hours.

Figure 3A:
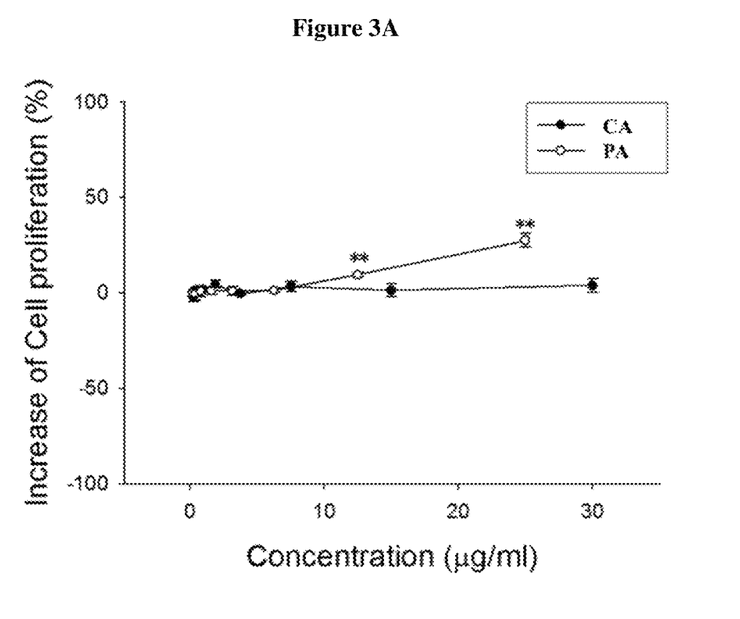
FIGS. 3A and 3B include charts showing the effect of *Plectranthus amboinicus* (PA) extract and *Centella asiatica* (CA) extract on endothelial cell proliferation as determined in an MTT assay (FIG. 3A) and on endothelial cell migration as determined in a scratch assay (FIG. 3B).

As shown in FIG. 3A, the PA extract enhanced cell proliferation, while the effect of CA on cell proliferation was not as good as the PA extract.

(ii) Scratch Assay—Migration

EA.hy926 endothelial cells were plated at a density of $8\times10^4$ cells/well in a 48-well plate for 24 hours. The confluent cell monolayer thus formed was scratched and treated with the PA or CA extract in a serum-free medium for 72 hour.

Figure 3B:
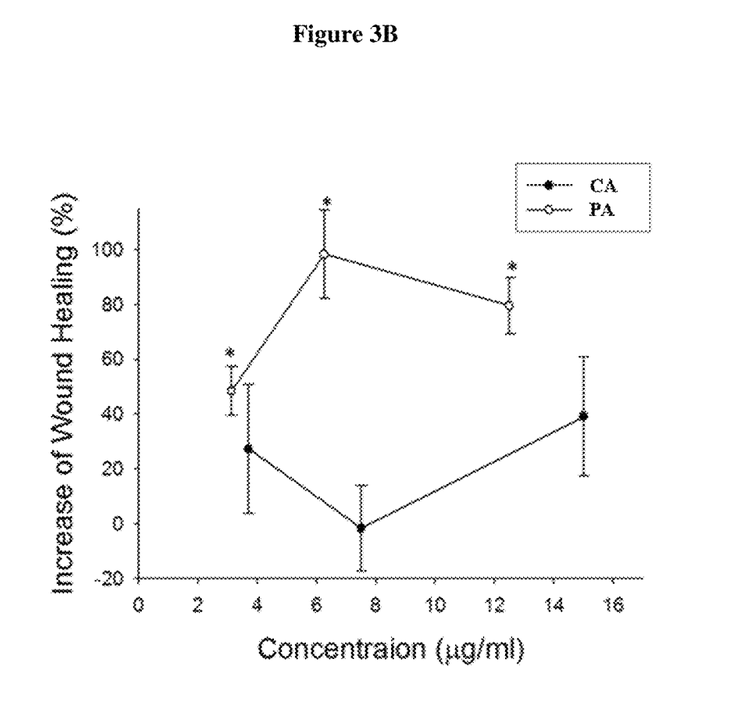

The results obtained from this study show that the PA extract significantly enhanced endothelial cell migration, which is essential to wound healing. Cells treated with the CA extract also showed signs of migration, but the result is not as significant as that of the PA extract. FIG. 3B.

Example 2: Effects of *Plectranthus Amboinicus* Extract and *Centella Asiatica* Extract on Keratinocytes Proliferation and Migration (i) SRB Assay—Proliferation The keratinocyte cell line, HaCaT cells, was used in this study. The cells were plated at a density of $4\times10^4$ cells/mL in 96-well plate for one day and then were treated with the PA or CA extract described in Example 1 above for 24 hours. After the treatment, the cells were fixed and stained with SRB dye.

Figure 4A:
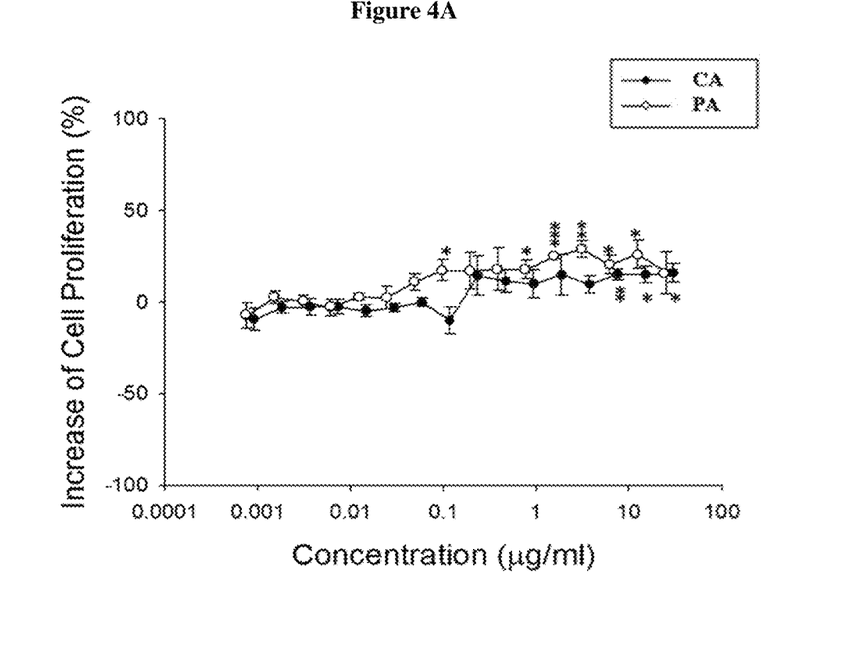
FIGS. 4A and 4B include charts showing the effect of *Plectranthus amboinicus* (PA) extract and *Centella asiatica* (CA) extract on keratinocyte cell proliferation as determined in an SRB assay (FIG. 4A) and on keratinocyte cell migration as determined in a scratch assay (FIG. 4B).
Figure 4B:
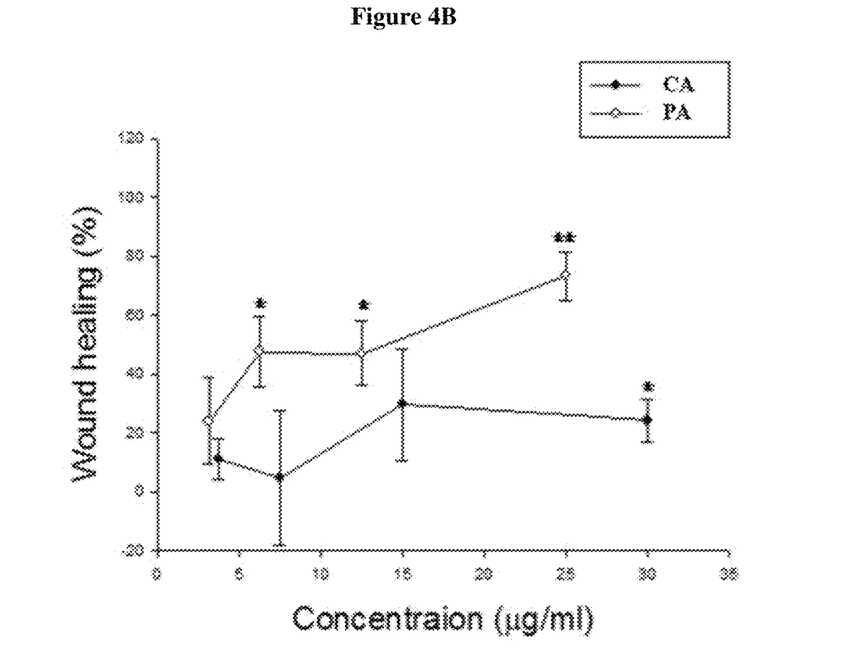

As shown in FIG. 4A, both PA and CA increase cell proliferation of keratinocyte cells.

(ii) Scratch Assay—Migration

HaCaT keratinocyte cells were plated at a density of $8\times10^4$ cells/well in a 48-well plate for one day. The confluent cell monolayer thus formed was scratched and treated with the PA or CA extract for 24 hour. The area of wound healing was quantified.

The results obtained from this study demonstrated that the PA extract induced cell migration (a wound healing effect) in keratinocytes in a dose-dependent manner. The CA extract also enhanced keratinocyte cell migration at a relatively high concentration (e.g., 30 µg/mL).

Example 3: Wound Healing Effect of Salvigenin and Asiaticoside

An in vitro capillary tube formation assay using human umbilical vein cells (HUVECs) was performed to examine the wound healing effect of salvigenin, an active agent of the PA extract disclosed herein.

Figure 5A:
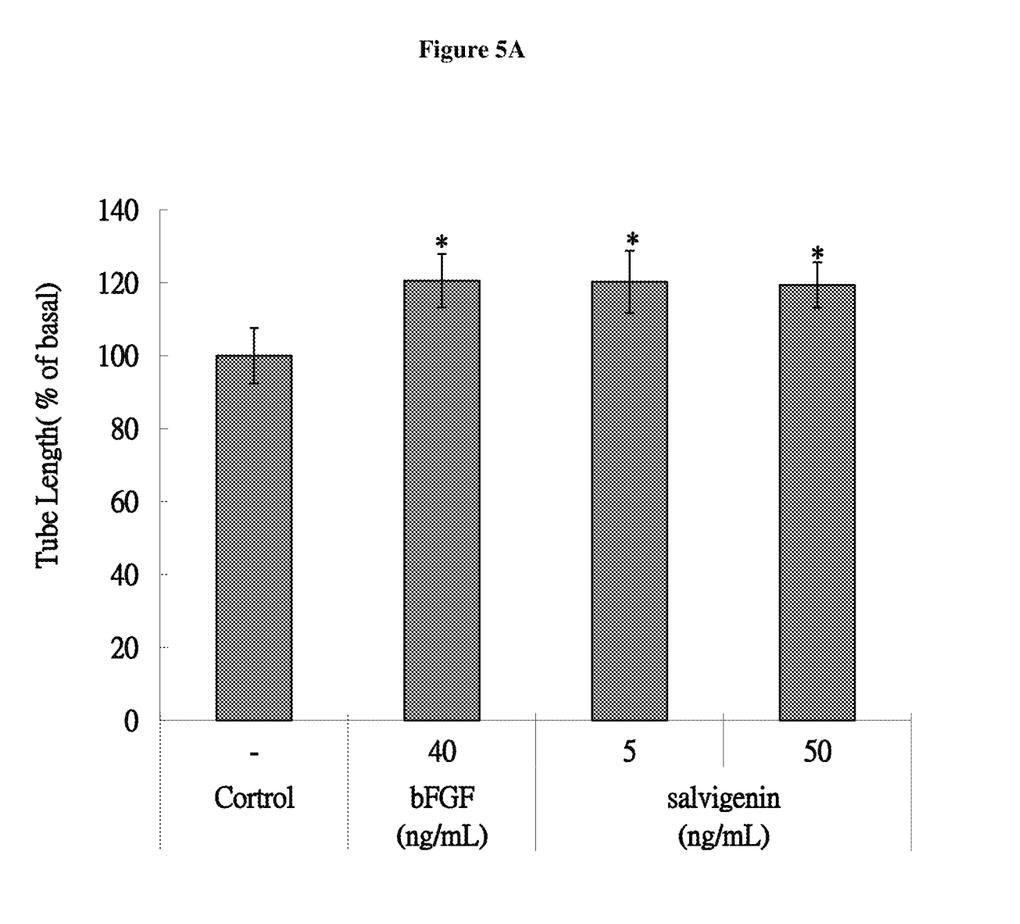
FIGS. 5A and 5B include a chart showing the effect of salvigenin in promoting wound healing in an in vitro capillary tube formation assay and a chart showing the effect of asiaticoside in promoting migration of keratinocytes.

Briefly, ninety-six-well Nunclon plates were coated with Matrigel (50 µL/well) and incubated at 37° C. for 30 min to promote gelling. HUVECs were cultured in M200 medium and cells between passages 2 and 4 were seeded (at $3\times10^5$ cells in 100 µL of medium) in each of the Matrigel-coated wells. A series of dilutions of testing compounds, as shown in FIG. 5A (including basic fibroblast growth factor (bFGF) as a positive control, and salvigenin), were added into the culture media to examine their biological effects on tube formation. After an 6 h incubation at 37° C. in a 5% CO2 humidified atmosphere, HUVECs were aspirated of media, fixed, and complete capillary tube networks within a designated area of a low-magnification (×10) field were photographed and counted with the aids of computer image software, ImagePro Plus V.4.5. The test data were expressed as the percentage of complete capillary tube formation relative to untreated HUVEC control cultures incubated under the same conditions.

As shown in FIG. 5A, salvigenin significantly increased tube formation by HUVEC cells.

To investigate the wound healing effect of asiatico side, a scratch migration assay was performed as follows. HaCaT keratinocyte cells were plated at a density of $8\times10^4$ cells/well in a 48-well plate for one day. The confluent cell monolayer thus formed was scratched and treated with the asiaticoside for 24 hour. The area of wound healing was quantified. The results obtained from this study demonstrated that the asiaticoside induced cell migration (a wound healing effect) in keratinocytes.

Figure 5B:
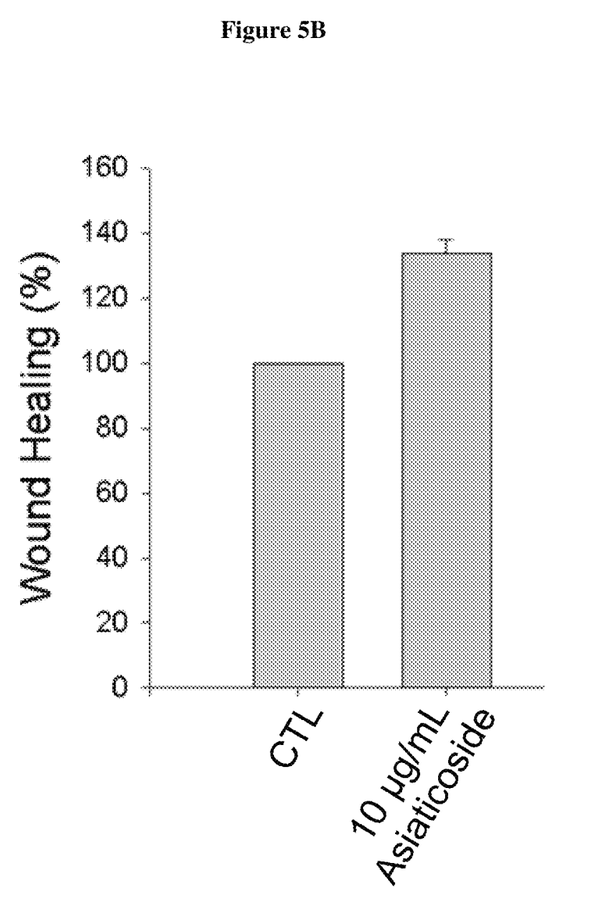

As shown in FIG. 5B, asiaticoside significantly promoted HaCaT cell migration, which would contribute to wound healing.

Example 4: Extracts of *Plectranthus Amboinicus* Promoted Normal Wound Healing

This study was performed to investigate the effect of various cream-based topical formulations including PA extract on normal wound closure in an animal model. Sprague-Dawley rats were randomly assigned into 4 groups. The rats were then anesthetized with pentobarbital and hairs on surgical area were removed. The skins on the dorsal medium areas in each rats were excised (full thickness) using surgical knife (2 cm×2 cm).

Rats of the four groups were treated with the following cream formulations, which were prepared according to the methods described herein:

G1: cream as a blank control,
G2: Winsolve-b ointment (from Yungshin Pharma, Co. LTD, Taiwan) as a reference control,
G3: Formulation I (1.25% PA extract), and
G4: Formulation II (0.25% PA extract).

The formulations were applied to each wound site twice a day and the wounds were covered with cheesecloth. The hoods were worn on the necks of the Sprague-Dawley rats (n=6; age 12 weeks) to prevent the wounds from receiving animal scratches. For wound closure measurement, the wound pictures were taken at day 4, 6, 8, 10, 12, 14 and 16. When taking pictures, a standard ruler was placed beside the wounds. Before analyzing the wounds with Image pro (Media cybernetics), length was standardized with the standard ruler in the picture to avoid the errors caused by different picturing distances.

Figure 6:
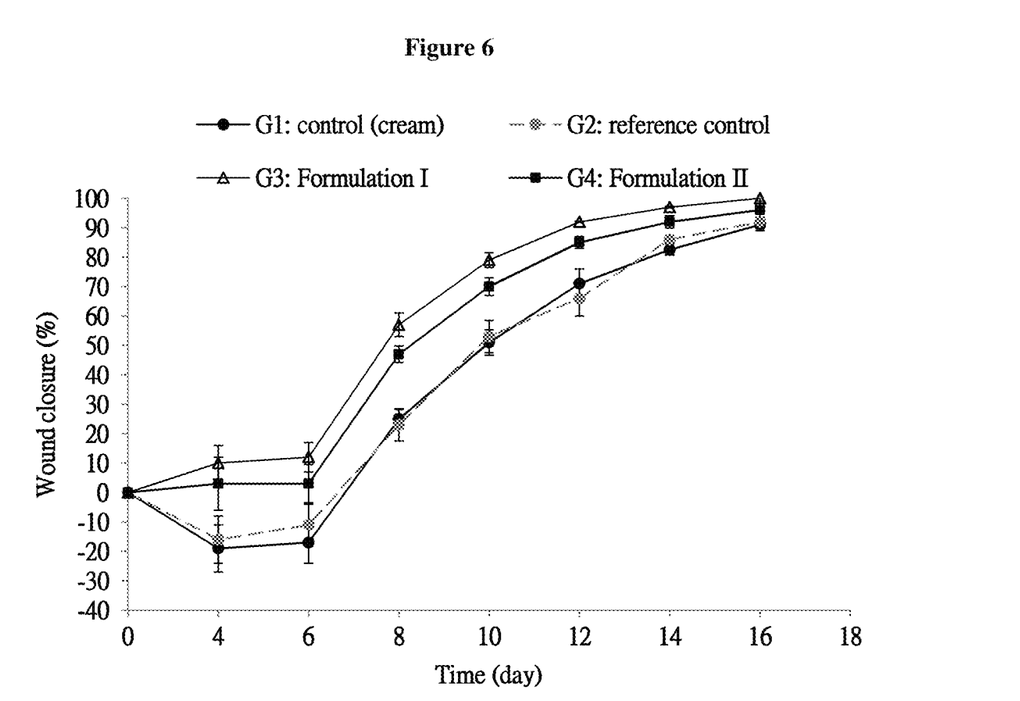
FIG. 6 is a chart showing the effect of *Plectranthus amboinicus* (PA) extract and *Centella asiatica* (CA) extract on normal wound healing in an animal model.

The results obtained from this study showed that Formulations I and II all showed promising effects in promoting wound closure in rats. Table 2 and FIG. 6.

TABLE 2

Wound Closure Effects

| Groups | CT50 (day)* |
|---|---|
| G1 (cream control) | 10 |
| G2 (reference control) | 9.9 |
| G3 (Formulation I) | 7.7 |
| G4 (Formulation II) | 8.3 |

*CT50: time (days) for 50% wound closure

Example 5: In Vivo Pharmacokinetic Study on a Topical Cream Comprising a *Plectranthus amboinicus* Extract and a *Centella asiatica* Extract Pharmacokinetic properties of a topical formulation containing extracts of *Plectranthus amboinicus* and *Centella asiatica* (1.25% in total, containing 0.0001% to 0.1% salvigenin by weight and 0.05% to 1% asiaticoside by weight) were evaluated in human patients having chronic diabetic foot ulcers (DFU). The PA and CA extracts in the topical formulation were prepared according to the methods described herein. The topical formulation is cream-based and further comprises cetostearyl alcohol (about 1.0-10% by weight, for example, about 3.5-6.5% by weight), white petrolatum and liquid petrolatum 350 cps (about 5%-30% by weight in total, for example, about 5-15% by weight in total), methyl paraben and propyl paraben (about 0.005% to 0.2% by weight in total, for example, 0.005-0.2% by weight in total), emulsifiers such as Span® 60 and Tween® 60 (about 0.5-10% by weight in total, for example, about 0.5-5% by weight in total), and one or more solvent such as propylene glycol (about 2-20% by weight, for example, about 4-10% by weight). The extracts were formulated in a cream-based topical formulation that additionally contains liquid petrolatum, propylene glycol, cetyl stearyl alcohol, white petrolatum, Span® 60, Tween® 60, propyl paraben, methyl paraben, and water.

A total of 12 patients completed the study. Each subject received one dose of the cream formulation on Day 1 followed by the blood sampling collection, then twice per day from Day 2 to Day 13, and a further blood sampling collection was scheduled on Day 14 after the final dose. Blood samples were analyzed for measuring plasma concentrations of salvigenin and asiaticoside, two active ingredients of the cream, by a validated LC/MS/MS methodology. The results obtained from day 1 showed that in the 12 patients, 2 patients had detectable plasma concentrations of salvigenin ≤12.403 pg/mL; and 5 patients had detectable plasma concentrations of asiaticoside ≤9.276 ng/mL.

The results obtained from day 14 showed that 4 out of the 12 patients had detectable plasma concentrations of salvigenin ≤16.972 pg/mL; and 5 out of the 12 patients had detectable plasma concentrations of asiaticoside ≤6.154 ng/mL.

Overall, the results obtained from this study showed that topical administrations of the topical formulation used in this clinical study resulted in limited systemic distribution of both salvigenin and asiaticoside.

A total of 6 adverse events (AEs) were reported by 3 patients. All AEs were deemed mild intensity, and those AEs were deemed "Unrelated" or "Unlikely related" to study treatment by the Investigator. On completion, 4 AEs were improved and 2 AEs were unchanged. There were no reports of significant AEs, death, or serious AEs.

Conclusion:

This 14-day study revealed that local application of the topical formulation used in this study resulted in limited systemic distribution of at least the active ingredients salvigenin and asiaticoside and is safe in DFU patients.

Example 6: Phase III Clinical Trial Using a Topical Cream Comprising a *Plectranthus amboinicus* Extract and a *Centella asiatica* Extract In an interim analysis, a total of 124 patients having DFU were randomized in a multi-center trial for evaluating the wound healing effect of the topical cream formulation described in Example 5 above. Inclusion and exclusion criteria for participation in the trial are listed below. Aquacel® Hydrofiber® dressing (ConvaTec, Princeton, N.J., USA) was used as a control treatment.

Selection Criteria

Inclusion Criteria for Patients

Patients were eligible for participation if all of the following criteria were met:
1. signed a written informed consent prior to the first study evaluation;
2. at least 20 and less than 80 years of age;
3. Diabetes mellitus (type 1 or 2) with an HbA1c<12.0% measured during screening or within three months prior to randomization;
4. an ankle brachial index on the target limb at least 0.8 measured during screening or within three months prior to randomization;
5. a target ulcer with the following characteristics:
   a. grade 1 or 2 per Wagner Ulcer Classification System;
   b. no higher than the ankle;
   c. no active infection;
   d. cross-sectional area of between 1 and 25 cm$^2$ post-debridement; and
   e. present for at least 4 weeks before randomization;
6. persons of childbearing potential had a negative pregnancy test and were not breastfeeding at screening visit; and
7. able and willing to attend the scheduled visits and comply with study procedures.

Exclusion Criteria

Patients were excluded from participation if any of the following were applicable:
1. presence of necrosis, purulence or sinus tracts not removable by debridement;
2. acute Charcot's neuroarthropathy as determined by clinical and/or radiographic examination;
3. underwent revascularization procedure aimed at increasing blood flow in the treatment target limb <4 weeks prior to randomization;
4. poor nutritional status defined as an albumin <2.5 g/dL;
5. AST and/or ALT >3 times the normal upper limit;
6. serum creatinine >2 times the normal upper limit;
7. treatment with immunosuppressive or chemotherapeutic agents, radiotherapy or systemic corticosteroids within the 4 weeks before randomization;
8. use of any investigational drug or therapy within the 4 weeks prior to randomization;
9. a psychiatric condition (e.g., suicidal ideation), current or chronic alcohol or drug abuse problem considered to pose a threat to compliance; or
10. judged by the investigator to be not suitable for the study for any other reason.

Discontinuation Criteria for Individual Patients

Patients were free to withdraw from the study for any reason and at any time without giving reason for doing so and without penalty or prejudice.

Additionally, patients were discontinued from the study if any of the following were applicable:
1. violation and/or significant deviation of study protocol;
2. lack of efficacy satisfactory (defined as a worsening of Wagner grade to level of 3);
3. safety concerns;
4. lost to follow-up;
5. withdrew consent;
6. if it was considered in the patient's best interest; or
7. termination of study by the sponsor.

Study Objectives and Outcomes

The primary objective of this study was to evaluate the use of the cream-based topical formulation on wound healing in human patients suffering from DFU.

The primary variable was the number of target ulcers healed in each group within 16 weeks. The primary efficacy outcome was the comparison of the incidence of complete healing of the target ulcer between the two treatment groups at the end of treatment.

For the purpose of this study a complete healing was defined as complete epithelialization which was maintained with no drainage for at least 2 weeks and confirmed by a blinded assessor.

The secondary efficacy outcomes were: time to complete ulcer healing (time of the original healing was taken as the time to healing); percentage change in ulcer surface area from baseline; percentage of subjects with a 50% reduction of ulcer surface area; and incidence of infection of the target ulcer.

Safety outcomes included assessment of the incidence of treatment-emergent adverse events, clinical laboratory values, and vital signs.

The exploratory endpoint was recurrence of the target ulcer within the follow-up period evaluated in those subjects who demonstrated complete wound healing at the end of comparison period.

Results

The wound healing efficacy of the diabetic patients treated with the topical cream formulation described in Example 5 or Aquacel®, was analyzed in the full analysis set (FAS) and the modified intent-to-treat (mITT) population. In the overall FAS and the mITT population, the results shown in Table 3 indicate that a higher percentage of patients treated with the topical formulation achieved complete ulcer healing as compared to the patients treated with Aquacel®. This result showed that the topical formulation used in this study was superior that Aquacel®, an existing product for treating wound healing, in at least complete ulcer healing, which is the primary endpoint of the study.

Further, subgroup analysis was performed in a patient population with baseline ulcer areas >5 cm$^2$ and plantar ulcers. This type of ulcer was known in the art as being difficult to recover. The results in Table 3 indicate that the complete healing rate of patients treated with the topical formulation was higher that the complete healing rate of patients treated with Aquacel®.

TABLE 3

Primary Endpoint: Complete Healing Rates

| Category | | Cream formulation Complete healing rate | Aquacel ® Hydrofiber ® Complete healing rate | P-value* |
|---|---|---|---|---|
| Overall | FAS | 60.3% | 34.4% | 0.004 |
| Overall | mITT | 62.7% | 32.2% | <0.001 |
| Subgroup of patients with baseline ulcer areas >5 cm$^2$ | mITT | 57.1% | 5.9% | 0.003 |
| Subgroup of patients with plantar ulcers | mITT | 63.6% | 24.1% | 0.002 |

*Chi-square test

Thus, the interim results from this Phase III clinical trial indicated that the topical cream formulation tested therein, comprising both PA and CA extracts, showed superior therapeutic effects in promoting wound healing in patients with DFU as relative to the Aquacel® Hydrofiber® control.

Other Embodiments

All of the features disclosed in this specification may be combined together in any manner. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents and published patent applications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A topical formulation, comprising:
   (i) an active agent comprising salvigenin in an amount of about 0.0001% to 0.5% (w/w) and asiaticoside in an amount of about 0.05% to 5% (w/w);
   (ii) a viscosity increasing agent in an amount of about 1.0-10% (w/w);
   (iii) an ointment base in an amount of about 5-30% (w/w);
   (iv) an antimicrobial preservative in an amount of about 0.005-0.2% (w/w); and
   (v) an emulsifying agent in an amount of about 0.5-10% (w/w);
   wherein the viscosity increasing agent comprises cetostearyl alcohol in an amount of about 3-7% (w/w);
   wherein the ointment base comprises liquid petrolatum and white petrolatum in a total amount of about 15-25% (w/w); and
   wherein the emulsifying agent comprises sorbitan monostearate and polysorbate 60 in a total amount of about 2-4% (w/w).

2. The topical formulation of claim 1, wherein the active agent is a *Plectranthus amboinicus* extract, a *Centella asiatica* extract, or a combination thereof, and wherein the *Plectranthus amboinicus* extract, the *Centella asiatica* extract, or the combination thereof comprises the salvigenin and asiaticoside.

3. The topical formulation of claim 2, wherein the *Plectranthus amboinicus* extract, the *Centella asiatica* extract, or the combination thereof is in an amount of about 0.1-30% (w/w) in the topical formulation.

4. The topical formulation of claim 1, wherein the topical formulation comprises salvigenin ranging from 0.0001% to 0.1% (w/w), and/or wherein the topical formulation comprises asiaticoside ranging from 0.05% to 1% (w/w).

5. The topical formulation of claim 1, wherein the active agent further comprises cirsimaritin, madecassoside, or a combination thereof.

6. The topical formulation of claim 2, wherein the *Plectranthus amboinicus* extract is prepared by contacting a whole *Plectranthus amboinicus* or a part thereof with a solvent having a polarity index lower than 7 to produce a solution and drying the solution to produce the *Plectranthus amboinicus* extract.

7. The topical formulation of claim 2, wherein the topical formulation comprises both the *Plectranthus amboinicus* extract and the *Centella asiatica* extract at a weight ratio of about 1:10 to 10:1.

8. The topical formulation of claim 1, wherein the viscosity increasing agent further comprises cholesterol, stearyl alcohol, chlorocresol, white wax, stearic acid, cetyl alcohol, or a combination thereof; and wherein the antimicrobial preservative comprises one or more paraben compounds.

9. The topical formulation of claim 1, wherein the ointment base is a cream base.

10. The topical formulation of claim 1, wherein the formulation further comprises one or more solvents.

11. The topical formulation of claim 10, wherein the one or more solvents comprise propylene glycol.

12. The topical formulation of claim 2, wherein the topical formulation comprises a combination of the *Plectranthus amboinicus* extract and the *Centella asiatica* extract in an amount of about 0.1-30% (w/w), cetostearyl alcohol in an amount of about 5-7% (w/w), a combination of white petrolatum and liquid petrolatum in a total amount of about 20% (w/w), a combination of methyl paraben and propyl paraben in a total amount of about 0.005-0.2% (w/w), and a combination of sorbitan monostearate and polysorbate 60 in a total amount of about 3% (w/w).

13. The topical formulation of claim 12, which further comprises propylene glycol in an amount of about 2-20% (w/w).

14. A method for promoting wound healing, comprising administering a topical formulation of claim 1 to a wound site of a subject in need thereof.

15. The method of claim 14, wherein the topical formulation is administered at least once per day.

16. The method of claim 14, wherein the subject is a human diabetic patient suffering from diabetic foot ulcer.

17. The method of claim 14, wherein the subject is a human patient having an open wound.

18. The method of claim 14, wherein the subject is a human patient having a chronic wound.

19. The method of claim 14, wherein the subject is a human patient having acne.

\* \* \* \* \*